United States Patent [19]

Turner et al.

[11] Patent Number: 4,751,334

[45] Date of Patent: * Jun. 14, 1988

[54] PROCESS FOR THE PRODUCTION OF BUTANE-1,4-DIOL

[75] Inventors: Keith Turner, Stockton-on-Tees; Mohammad Sharif, Middlesbrough; Colin Rathmell, Yarm; John W. Kippax, Bedale; Anthony B. Carter, Stockton-on-Tees; John Scarlett, Spennymoor; Arthur J. Reason, Middlesbrough; Norman Harris, Norton, all of England

[73] Assignee: Davy McKee (London) Limited, London, England

[*] Notice: The portion of the term of this patent subsequent to Apr. 22, 2003 has been disclaimed.

[21] Appl. No.: 901,450

[22] PCT Filed: Nov. 18, 1985

[86] PCT No.: PCT/GB85/00524

§ 371 Date: Jul. 21, 1986

§ 102(e) Date: Jul. 21, 1986

[87] PCT Pub. No.: WO86/03189

PCT Pub. Date: Jun. 5, 1986

Related U.S. Application Data

[63] Continuation-in-part of Ser. No. 673,797, Nov. 21, 1984, Pat. No. 4,584,419.

[30] Foreign Application Priority Data

Jun. 4, 1985 [GB] United Kingdom ................ 8514002

[51] Int. Cl.⁴ ..................... C07C 29/136; C07C 31/20
[52] U.S. Cl. ..................................... 568/864; 549/326
[58] Field of Search ......................................... 568/864

[56] References Cited

U.S. PATENT DOCUMENTS

| | | | |
|---|---|---|---|
| 2,130,501 | 9/1938 | Lazier | 568/864 |
| 3,772,395 | 11/1973 | Yamaguchi et al. | 568/864 |
| 4,032,458 | 6/1977 | Couley et al. | 568/864 |
| 4,112,245 | 9/1978 | Zehner | 568/864 |
| 4,155,919 | 5/1979 | Ramioulle et al. | 568/864 |
| 4,551,565 | 11/1985 | Miyazaki et al. | 568/864 |
| 4,584,419 | 4/1986 | Sharif et al. | 568/864 |
| 4,611,085 | 9/1986 | Kitson | 568/864 |

Primary Examiner—J. E. Evans
Attorney, Agent, or Firm—Bernard, Rothwell, & Brown

[57] ABSTRACT

Butane-1,4-diol is produced by vapor phase hydrogenolysis of an alkyl ester of a $C_4$ dicarboxylic acid, e.g. diethyl maleate, over a reduced Cu-Cr or Cu-Zn mixed oxide catalyst. Two adiabatic hydrogenolysis zones are used. The mixture exiting the first of these zones is cooled (by, for example, 5° C.) and the resulting cooled mixture is fed to the second zone in which is reequilibriates at a lower temperature to increase the butane-1,4-diol yield at the expense of gamma-butyrolactone. Typical reaction conditions include use of temperatures of 150° C. to 200° C., pressures of 25 to 70 bar, and a $H_2$:ester molar ratio of 100:1 to 800:1. When using a maleate ester it is often advantageous to hydrogenate this to the corresponding succinate ester in an upstream hydrogenation zone prior to entry to the first hyrogenolysis zone.

16 Claims, 1 Drawing Sheet

U.S. Patent    Jun. 14, 1988    4,751,334
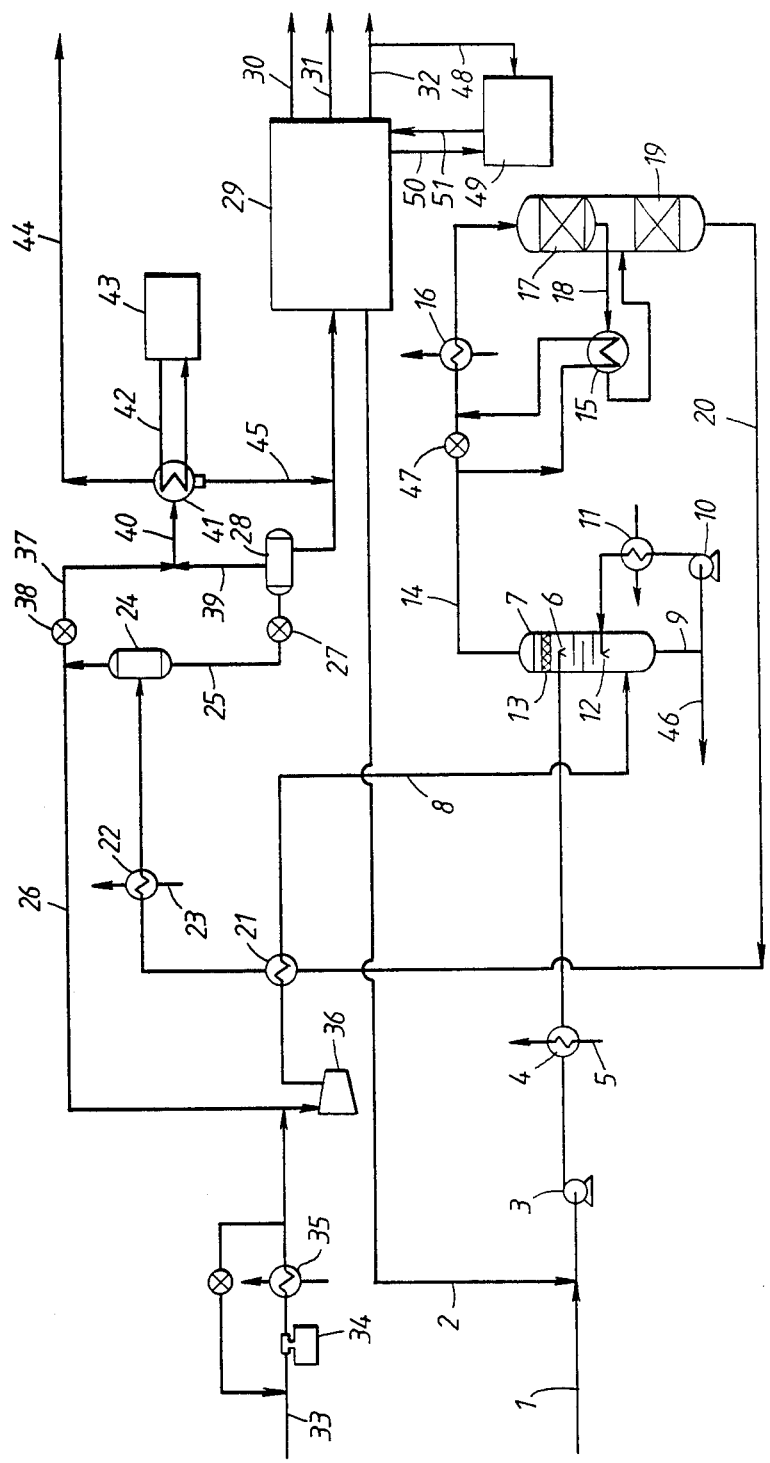

PROCESS FOR THE PRODUCTION OF BUTANE-1,4-DIOL

This application, which is the National Stage of International Appln. No. PCT/GB85/00524, filed Nov. 18, 1985, is a continuation-in-part of U.S. application Ser. No. 673,797, filed Nov. 21, 1984 by Mohammad Sharif and Keith Turner for PROCESS, now U.S. Pat. No. 4,584,419, issued Apr. 22, 1986.

This invention relates to a process for the production of butane-1,4-diol, more particularly to a process for the production of butane-1,4-diol by hydrogenolysis of a dialkyl ester, usually a di-($C_1$ to $C_4$ alkyl) ester, of a $C_4$ dicarboxylic acid, such as maleic acid, fumaric acid, or succinic acid.

Butane-1,4-diol is used as a monomer in the production of plastics such as polybutylene terephthalate. It is also used as an intermediate for manufacture of butyrolactone and of the important solvent, tetrahydrofuran.

The most commonly adopted present method of manufacturing butane-1,4-diol involves reacting acetylene and formaldehyde by the Reppe reaction to give but-2-yne-1,4-diol which is then hydrogenated to form butane-1,4-diol.

Alternatively it has been proposed in EP-B-0018163 to react allyl alcohol, which can be produced from propylene, with iso-butylene to form allyl t-butyl ether. This compound is then hydroformylated using, for example a rhodium complex hydroformylaton catalyst, to give 4-t-butoxybutyraldehyde, which is then hydrogenated and cleaved under mild conditions with the aid of an acid catalyst to give butane-1,4-diol and iso-butylene which is recycled for reaction with further allyl alcohol.

There have also been a number of proposals to produce butane-1,4-diol from maleic anhydride. According to these proposals maleic anhydride, which is produced by oxidation of butane or benzene, is esterified to give a diester of maleic acid which is then hydrogenated in one or more stages to give butane-1,4-diol. Alternatively it is proposed that, maleic acid or anhydride should be directly hydrogenated. In some of these proposals butyrolactone is an intermediate product.

U.S. Pat. No. 4,001,282 describes a process for production of butyrolactone by passing vaporised maleic acid, maleic anhydride, or a mixture thereof together with water and hydrogen over a metallic catalyst capable of hydrogenolysing a carboxylic group to a hydroxymethyl group. Typical catalysts include copper-zinc catalysts (such as Girdler G-66 ARS and G-66-BRS) and copper chromite catalysts (such as Girdler G-13). Besides butyrolactone the reported products include succinic acid anhydride, propionic acid, butyric acid, propanol and n-butanol, but no mention is made of butane-1,4-diol.

U.S. Pat. No. 4,048,196 teaches production of butane-1,4-diol and/or tetrahydrofuran by multi-stage catalytic hydrogenaton of maleic anhydride or succinic anhydride. In a first liquid phase hydrogenation step maleic anhydride or succinic anhydride is hydrogenated over a nickel catalyst to give butyrolactone. This is then hydrogenated in the liquid phase over a copper/zinc oxide or hydroxide catalyst to give butane-1,4-diol and tetrahydrofuran.

In U.S. Pat. No. 4,083,809, U.S. Pat. No. 4,105,674 and GB-A-1534136 there is described a process for producing butyrolactone using a Cu-Pd catalyst for vapour phase hydrogenation of maleic acid, succinic acid, their anhydrides, and mixtures of two or more thereof.

U.S. Pat. No. 2,079,414 describes use of copper chromite as a catalyst for effecting hydrogenation of esters. It is recommended that, in operating in the vapour phase, temperatures within the range of 300° C. to 400° should be used. Diethyl succinate is mentioned.

U.S. Pat. No. 2,040,944 recommends use of temperatures of 230° to 400° C. for hydrogenation of esters of non-aromatic polybasic acids with a monohydric aliphatic alcohol containing at least four carbon atoms. it recommends copper chromite as catalyst and teaches that the catalyst can be prepared by ignition of a copper ammonium chromate precipitate and used without further treatment or after reduction by hydrogen at a temperature of 500° C. or higher. It goes on to mention that either the liquid phase or vapour phase can be used, depending largely upon the ester to be hydrogenated. Pressures of 100 to 250 bar are recommended, as well as use of about 5 to 20 moles of hydrogen per mole of ester. Example 1 describes a liquid phase batch reaction in which crude butyl succinate is hydrogenated at 3000 p.s.i.g. (207 bar) at 255° C. using a copper chromite catalyst.

A discussion of the use of copper chromite as a catalyst for hydrogenation of esters is to be found in "Organic Reactions", Vol. 8, published in 1954 by J. Wiley and Sons, Inc.. Chapter 1 of this reference book is by Homer Adkins and is entitled "Catalytic Hydrogenation of Esters to Alcohols". Table II on page 15 lists two experiments in which diethyl succinate is reacted at 5000 p.s.i. (345 bar) and 150° C. for 4 hours and at 3300 p.s.i. (227.5 bar) and 250° C. for 6.5 hours respectively. This reference suggests that the "copper chromite" catalyst is more correctly described as an approximately equimolecular combination of cupric oxide and cupric chromite, i.e. $CuO$, $CuCr_2O_4$.

Production of copper chromite catalysts for use in hydrogenation of esters is described in FR-A-1276722. This recommends use of ester hydrogenation conditions including use of temperatures of between 100° C. and 350° C., preferably between 200° C. and 300° C., and hydrogen pressures between "50 hpz and 500 hpz" (by which is presumably meant between 50 bar and 500 bar).

Production of butane-1,4-diol and tetrahydrofuran by a process in which a dialkyl maleate is subjected to hydrogenolysis in the liquid phase in the presence of a copper chromite catalyst is described in GB-A-1454440 and GB-A-1464263. A similar liquid phase process using nickel-based catalysts is described in GB-A-1587198.

Hydrogenation of a di-($C_1$ to $C_7$ alkyl) succinate at 100 to 300 atmospheres and 200° C. to 260° C. over a copper chromite catalyst to produce butane-1,4-diol is described in DE-A-2719867.

U.S. Pat. No. 4,172,961 describes in Example 1 experiments in which a mixture of dibutyl butoxysuccinate, dibutyl maleate and dibutyl fumarate is hydrogenated using a copper chromite catalyst at 2000 psig to 4000 psig (141.65 bar to 282.26 bar and at a temperature of 250° C. to yield butane-1,4-diol.

A two stage hydrogenation procedure in which a dialkyl maleate is hydrogenated first to the corresponding dialkyl succinate in a first hydrogenation zone and then the resulting dialkyl succinate is hydrogenated to yield butane-1,4-diol in a second hydrogenation zone is described in U.S. Pat. No. 4,032,458. Copper chromite is suggested as the catalyst for use in both hydrogenation zones; use of temperatures of about 100° C. to about 200° C. and hydrogen pressures of about 2000 psig to about 3500 psig (about 141.65 bar to about 247.11 bar) in the first hydrogenation is recommended, whilst use of temperatures of about 225° C. to about 300° C. and pressures of about 3000 psig to about 4000 psig (about 241.95 bar to 282.26 bar) in the second hydrogenation zone is said to provide the necessary severity of operating conditions required to convert substantially all of the dialkyl esters to a product comprising butane-1,4-diol and monohydric alkanol.

Butyrolactone is produced, according to GB-A-1168220, by vapour phase hydrogenation of maleic anhydride, succinic acid, an ester of maleic acid, an ester of succinic acid, or an ester of fumaric acid in the presence of a copper-zinc catalyst to which may be added small amounts of one or more promoters other than chromium. This specification mentions that the preparation of butyrolactone by hydrogenation of the chosen starting materials was already known and states (see page 1, lines 23 to 25):

"It is also possible to carry out the hydrogenation in the vapour phase when the preferred catalyst is copper chromite."

GB-A-1168220 continues (see page 1, lines 29 to 39):

"Furthermore hitherto known hydrogenation processes in the vapour phase suffer from the disadvantage of having to be carried out at a relatively high temperature, for example, about 300° C., and moreover in order to obtain a good conversion rate, the reaction material should be fed to the catalyst at low speed. It is also difficult to reactivate the copper-chromite catalyst, when the activity has been lowered by use for a period of time."

It is an object of the present invention to provide a novel improved process for the production of butane-1,4-diol using as a starting material a precursor that can be produced from maleic anhydride and hence ultimately from butane or benzene as feedstock.

According to the present invention there is provided a process for the production of butane-1,4-diol which comprises:

providing first and second hydrogenolysis zones, each containing a charge of a heterogeneous ester hydrogenolysis catalyst;

supplying to the first hydrogenolysis zone at an elevated pressure and at an elevated first feed temperature in excess of the threshold temperature for the hydrogenolysis reaction a vaporous feed stream comprising a dialkyl ester of a $C_4$ dicarboxylic acid in vapour form and excess hydrogen;

allowing the ester to undergo hydrogenolysis in the first hydrogenolysis zone under substantially adiabatic reaction conditions thereby to form a vaporous first reaction mixture that is substantially free from the starting ester and contains, in addition to unreacted hydrogen, butane-1,4-diol and gamma-butyrolactone in a first molar ratio;

cooling the vaporous first reaction mixture;

supplying a second vaporous feed stream comprising resulting cooled vaporous first reaction mixture to the second hydrogenolysis zone at a second feed temperature in excess of the threshold temperature for the hydrogenolysis reaction;

allowing the second vaporous feed stream to react further and to equilibrate under substantially adiabatic reaction conditions in the second hydrogenolysis zone; and recovering from the second hydrogenolysis zone a vaporous second reaction mixture containing, in addition to unreacted hydrogen, butane-1,4-diol and gamma-butyrolactone in a second molar ratio that is greater than the first molar ratio.

Preferably the hydrogenolysis catalyst comprises copper chromite. It is especially preferred to use a reduced copper chromite catalyst which contains, before reduction, from about 25 to about 45% by weight of copper and from about 20 to about 35% by weight of chromium.

Preferably the ester is a di-($C_1$ to $C_4$ alkyl) ester of a but-2-en-1,4-dioic acid or of succinic acid.

In operating the process of the invention with a copper chromite catalyst it is preferred to operate at a temperature no higher than about 200° C. Hence the first feed temperature preferably lies in the range of from about 150° C. to about 200° C., and even more preferably in the range of from about 170° C. to about 190° C. The two hydrogenolysis zones are each operated substantially adiabatically. The first reaction mixture thus exits the first hydrogenolysis zone at a temperature above the first inlet temperature. The second inlet temperature at which the cooled vaporous first reaction mixture is supplied as second vaporous feed mixture to the second hydrogenolysis zone is preferably at least about 5° C. lower than the temperature at which the vaporous first reaction mixture exits the first hydrogenolysis zone. Typically the second inlet temperature is at least about 10° C. lower, e.g. about 15° C. lower, than the exit temperature from the first hydrogenolysis zone. The extent of cooling between the two hydrogenolysis zones will in no case be so much as to cause condensation of condensible products upon entry to the second hydrogenolysis zone. In most cases it is unlikely that the second inlet temperature will be more than about 25° C. lower than the exit temperature from the first hydrogenolysis zone.

The operating pressure is preferably at least about 25 bar but not more than about 70 bar, and is most preferably in the range of from about 35 bar to about 45 bar. Usually it is at least about 30 bar.

The two hydrogenolysis zones may each comprise a separate reactor which is operated under substantially adiabatic conditions. Alternatively the two hydrogenolysis zones may comprise separate beds of catalyst in the same reactor vessel.

The dialkyl ester of a $C_4$ dicarboxylic acid used in the process of the invention is preferably derived from an alkyl alcohol containing from 1 to 4 carbon atoms. Examples of such esters include diethyl maleate, diethyl fumarate, diethyl succinate, and mixtures of two or more thereof. Other suitable esters include the di-methyl, di-n-propyl, di-i-propyl, di-n-butyl, di-i-butyl, and di-sec-butyl esters of maleic, fumaric and succinic acids, as well as mixtures thereof. Preferably the ester is selected from diethyl maleate, diethyl fumarate, diethyl succinate, and mixtures of two or more thereof.

Besides using an undiluted ester as feedstock it is also possible to use a solution of the ester in a suitable inert solvent, e.g. methanol, ethanol, or n- or iso-propanol.

It is desirable to pretreat the ester feedstock, e.g. by distillation, so as to remove substantially all of any sulphurous or halogenated impurities present in the feedstock. It is also preferred to remove substantially all water therefrom.

The ester or ester solution feed can be admixed with recycled ester recovered in the product recovery section of the plant. If a di-($C_1$ to $C_4$ alkyl) maleate or fumarate is used as starting material, then the product stream from the second hydrogenolysis zone may include a minor amount of the corresponding dialkyl succinate; this can be recycled from the product recovery section of the plant for admixture with the di-($C_1$ to $C_4$ alkyl) maleate or fumarate or solution thereof used as fresh feed supplied to the first hydrogenolysis zone. If the sole desired product is butane-1,4-diol, then all of any co-product gamma-butyrolactone can be recycled from the product recovery section for admixture with fresh feed ester or ester solution. Often, however, a ready market can be found for most if not all of the co-product gamma-butyrolactone. The plant operator can in this case adjust the output of the plant to meet market requirements either by adjusting the operating temperatures of the hydrogenolysis zones or by recycling a part of the butane-1,4-diol product or a part of the byproduct gamma-butyrolactone from the product recovery section for admixture with the ester or ester solution feed.

The process requires that the starting ester and any other condensible component present be in the vapour phase in the first and second hydrogenolysis zones. This means that the composition of the vaporous mixture must be controlled so that, under the selected operating conditions, the temperature of the mixture in contact with the catalyst is always above the dew point of the ester and of any other condensible component present. The temperature of the mixture in contact with the catalyst is at all times preferably at least about 5° C., more preferably at least about 10° C., and even more preferably at least about 15° C., higher than the dew point of the mixture. This can normally be achieved by selecting an appropriate gas:ester ratio in the vaporous mixture. A convenient method of forming a vaporous mixture for use in the process of the invention is to spray the liquid ester or ester solution into a stream of hot hydrogen-containing gas so as to form a saturated or partially saturated vaporous mixture. Alternatively such a vaporous mixture can be obtained by bubbling a hot hydrogen-containing gas through a body of the liquid ester or ester solution. If a saturated vapour mixture is formed it should then be heated further or diluted with more gas so as to produce a partially saturated vaporous mixture prior to contact with the catalyst.

Reduction of a maleate or fumarate ester to butane-1,4-diol involves reaction of 5 moles of $H_2$ with each mole of ester, according to the following equation:

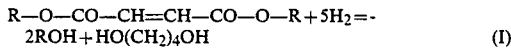

(I)

where R is an alkyl radical containing from 1 to 4 carbon atoms.

However, when a succinate ester is hydrogenolysed, only 4 moles of $H_2$ are consumed:

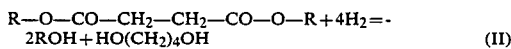

(II)

where R is as defined above.

The vaporous mixture will normally contain excess hydrogen. It may additionally contain a minor amount of carbon oxides. The vaporous mixture may further include vaporised inert sovent (if used) and one or more inert gases (e.g. $N_2$, A, $CH_4$ etc) which may be present in the hydrogen supply in a major or minor amount. It may also include vaporous material recycled from the product recovery section. Preferably the hydrogen supply is substantially free from sulphur compounds, from halogens such as $Cl_2$, and from halogen-containing compounds such as HCl.

In the vaporous mixture the $H_2$:ester molar ratio is typically at least about 100:1 up to about 800:1 or more. Preferably it is at least about 200:1 up to about 500:1. The presence of the excess hydrogen and of any inert gases that may be present helps to moderate the temperature rise in the first hydrogenolysis zone.

In practice the reduction of a maleate ester, such as diethyl maleate, is more complex than is suggested by equation (I) above and results in production of variable amounts of by-products, including tetrahydrofuran, gamma-butyrolactone and n-butanol. Although the reaction mechanism has not been fully elucidated yet, the currently available evidence is consistent with the following sequence:-

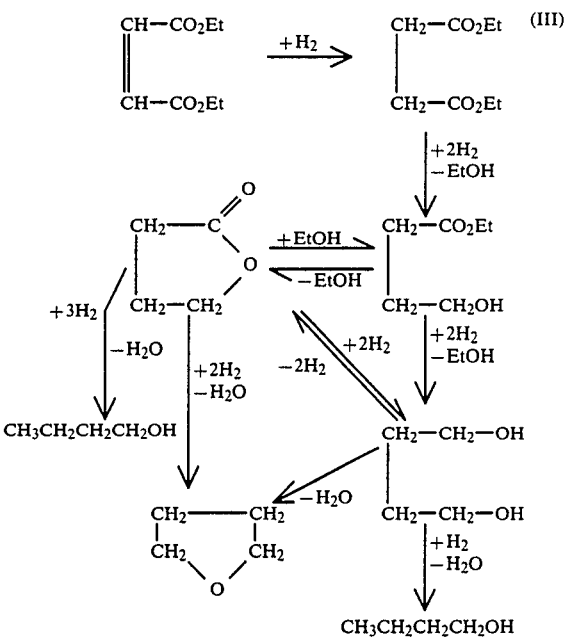

The preferred catalyst used in the first and/or second hydrogenolysis zone is a reduced copper chromite catalyst. This should be prepared by careful reduction of copper chromite prior to use. Preferably the catalyst is reduced at a temperature of not more than about 200° C., for an extended period using a mixture of $H_2$ and an inert gas, such as nitrogen, methane or argon. A typical gas used for reduction of the catalystis an $H_2$ in $N_2$ mixture containing, for example, from about 1% up to about 15% by volume of $H_2$. Usually the catalyst is reduced for at least about 24 hours prior to use. Best results are obtained when reduction is effected for several days at a temperature of from about 120° C. to about 180° C. prior to use in the process of the invention. It will usually be unnecessary to exceed about 10 days reduction pretreatment. If the catalyst is reduced at a temperature in excess of about 200° C., the activity is noticeably inferior to the activity obtained by reduction at lower temperatures. If the catalyst is supplied in pre-reduced form then the period of reduction can be shorter. In the later stages of pre-treatment higher $H_2$ concentrations can be used; thus $H_2$ can replace the $H_2/N_2$ mixture towards the end of the reduction pretreatment. It is best to use an elevated pressure during this pre-treatment period; for example, pressures of from 1 bar up to about 50 bar or higher can be used. After the reduction treatment the catalyst should be maintained under an inert gas, a hydrogen/inert has mixture or hydrogen until use.

The formula of copper chromite may be written as $CuCr_2O_4$. However, it is known that copper chromite is non-stoichiometric and some authors have, for example, described a copper chromite catalyst as copper chromium oxide of the formula $CuO \cdot CuCr_2O_4$. Thus the catalyst may contain an excess of copper oxide. It may further or alternatively contain a minor amount of at least one stabilizer, such as barium or manganese. The catalyst contains, before reduction, from about 25 to about 45% by weight of copper and from about 20 to about 35% by weight of chromium. The most preferred catalysts are those containing from about 32 to about 38% by weight of copper and from about 22 to about 30% by weight of chromium. Such catalysts preferably contain no more than about 15% by weight of a stabilizer or stabilizers, if present. It may be supported on a suitable inert carrier. Desirably the catalyst is in finely divided form having an internal surface area, as measured by the well-known BET method, of at least about 30 sq. m. per gram and preferably at least about 60 sq. m. per gram. Preferably it is formed into cylindrical pellets or into other conventional catalyst shapes, such as rings, saddles, or the like.

Other catalysts that may be used in the first and/or second hydrogenolysis zone of the process of the invention include a reduced copper oxide/zinc oxide catalyst of the type disclosed in WO-A-82/03854.

The ester is preferably supplied to the first hydrogenolysis zone at a rate corresponding to a liquid hourly space velocity in the range of from about 0.1 $hr^{-1}$ up to about 0.6 $hr^{-1}$ or higher, for example up to about 1.5 $hr^{-1}$ or even up to about 3.0 $hr^{-1}$. By the term "liquid hourly space velocity" we mean the number of unit volumes of the liquid ester supplied to the vaporization zone per unit volume of catalyst per hour. This normally corresponds to a gaseous hourly space velocity in the range of from about 2500 $hr^{-1}$ up to about 160,000 $hr^{-1}$, for example up to about 85,000 $hr^{-1}$, most preferably in the range of from about 8000 $hr^{-1}$ To about 30,000 $hr^{-1}$. By the term "gaseous hourly space velocity" we mean the number of unit volumes of vaporous mixture measured at 1 bar and 0° C. passed over a unit volume of catalyst per hour.

Usually the feed temperature to the second hydrogenolysis zone is not more than about 175° C. and even more preferably lies in the range of from about 160° C. to about 175° C.

If desired further gas and/or ester can be admixed with the product stream from the first hydrogenolysis zone prior to admission to the second hydrogenolysis zone in order to adjust the temperature or the $H_2$:ester molar ratio. It is also contemplated that one or more materials recovered from the product recovery section of the plant (e.g. dialkyl succinate, unreacted dialkyl maleate or fumarate, gamma-butyrolactone and/or butane-1,4-diol) can be admixed with the product stream from the first hydrogenolysis zone prior to admission to the second hydrogenolysis zone, instead of or in addition to recycling such material to the inlet end of the first hydrogenolysis zone.

The reduction of a di-($C_1$ to $C_4$ alkyl) maleate to the corresponding di-($C_1$ to $C_4$ alkyl) succinate according to equation (III) above is an exothermic reaction. As the yield of by-product tetrahydrofuran is found to be dependent upon the maximum temperature to which the reaction mixture is exposed in the hydrogenolysis zones and upon the residence time at elevated temperatures, it is preferred to use a di-($C_1$ to $C_4$ alkyl) succinate as the ester supplied to the first hydrogenolysis zone or as a major component thereof, rather than the corresponding di-($C_1$ to $C_4$ alkyl) maleate or fumarate, since this results in production of a correspondingly smaller temperature rise in the first hydrogenolysis zone and hence in production of a smaller proportion of by-product tetrahydrofuran. Hence, in a particularly preferred process according to the invention a di-($C_1$ to $C_4$ alkyl) maleate or fumarate, such as diethyl maleate or fumarate, is hydrogenated to the corresponding di-($C_1$ to $C_4$ alkyl) succinate, such as diethyl succinate, in a hydrogenation zone upstream from the first hydrogenolysis zone using a catalyst which either has little or no ester hydrogenolysis activity or which is maintained under conditions such that ester hydrogenolysis and formation of butane-1,4-diol are minimised. Prior to entry to the first hydrogenolysis zone, the di-($C_1$ to $C_4$ alkyl) succinate-containing reaction mixture from the upstream hydrogenation zone is cooled, if necessary, prior to entry to the first hydrogenolysis zone in order to remove the heat of hydrogenation of the C:C bond of the maleate or fumarate ester prior to entry to the first hydrogenolysis zone. In this way the temperature rise in the first hydrogenolysis zone is kept as small as possible and the production of by-product tetrahydrofuran is thereby minimised.

As examples of catalysts that can be used in the upstream hydrogenation zone when using a di-($C_1$ to $C_4$ alkyl) maleate or fumarate, there can be mentioned, for example, copper oxide/zinc oxide catalysts of the type disclosed in WO-A-82/03854, supported nickel, palladium, ruthenium, and cobalt hydrogenation catalysts, zinc oxide, copper chromite catalysts, and copper chromite catalysts which have been deliberately deactivated to reduce their ester hydrogenolysis characteristics. When using copper chromite catalysts, which may or may not have been deactivated, it is expedient to supply the di-($C_1$ to $C_4$ alkyl) maleate or fumarate to the upstream hydrogenation zone at a relatively high rate, for example at a rate corresponding to a liquid hourly space velocity of at least about 1.0 $hr^{-1}$, preferably from about 3.0 $hr^{-1}$ to about 6.0 $hr^{-1}$.

For convenience and ease of construction and operation of the plant it is preferred to operate any upstream hydrogenation zone for conversion of dialkyl maleate and/or fumarate to dialkyl succinate at substantially the same pressure as is used in the first and second hydrogenolysis zones. Hence typical operating pressures in the upstream hydrogenation zone range from about 25 bar to about 70 bar and preferably lie in the range of from about 35 bar to about 45 bar. Vapour phase hydrogenation conditions are usually selected in the upstream hydrogenation zone. The inlet temperature to the upstream hydrogenation is preferably kept as low as is practicable consistent with use of vapour phase conditions and is typically in the range of from about 160° C. to about 180° C. The volume of catalyst in the upstream hydrogenation zone is selected to provide the desired high rate of ester throughput.

The reaction mixture exiting the upstream hydrogenation zone is supplied as feed mixture to the first hydrogenolysis zone. Prior to introduction to the first hydrogenolysis zone the reaction mixture exiting the upstream hydrogenation zone is cooled somewhat so as to enable as low an inlet temperature as possible to be used in the first hydrogenolysis zone and thereby limit the maximum temperature achieved therein. Further hydrogen and/or fresh feed ester and/or one or more materials recycled from the product recovery zone may be admixed with the reaction mixture from the upstream hydrogenation zone prior to its introduction into the first hydrogenolysis zone.

The product mixture exiting the second hydrogenolysis zone contains, in addition to unreacted hydrogen and possibly other gases, a mixture of condensible materials including butane-1,4-diol and alkyl alcohol (e.g. a $C_1$ to $C_4$ alkyl alcohol) derived from the alkyl moiety of the dialkyl ester starting material. The condensible materials may further include butyrolactone, dialkyl succinate and possibly also a small amount of unreacted ester and minor amounts of by-products, including n-butanol and tetrahydrofuran. These condensible materials are preferably condensed from the product mixture and separated in any suitable fashion, e.g. by distillation in one or more stages under normal, elevated or reduced pressure. In designing a suitable product recovery system, it should be borne in mind that some of the components present in the product mixture are capable of forming azeotropic mixtures with one or more other components of the product mixture. The liquid butane-1,4-diol product and any butyrolactone formed can be passed forward for purification whilst any minor by-products can be used as fuel for the process. The alkyl alcohol can be recycled for reaction with further maleic or succinic anhydride or with further maleic acid, fumaric acid, or succinic acid to form fresh dialkyl $C_4$ dicarboxylic acid ester for use in the process of the invention. Any unreacted starting ester (e.g. dialkyl maleate) and/or intermediate ester (e.g. dialkyl succinate) can be recycled for admixture with the ester or ester solution feed. If desired some of the butane-1,4-diol, and/or gamma-butyrolactone byproduct, can be recycled for admixture with the product stream from the first hydrogenolysis zone.

The unreacted hydrogen-containing gases from the product recovery step can be recycled. Purge lines can be used to control the level of inerts and/or byproducts in the circulating gas stream and in any liquid recycle line.

In order that the invention may be clearly understood and readily carried into effect a preferred form of plant designed to operate a process in accordance with the invention will now be described, by way of example only, with reference to the accompanying drawing which is a flow diagram of a plant for effecting hydrogenolysis of diethyl maleate.

It will be appreciated by those skilled in the art that, as the drawing is diagrammatic, many further items of equipment, such as temperature and pressure sensors, valves, control equipment, and the like, will be required in a commercial plant. The provision of such ancillary items of equipment forms no part of the present invention and will be in accordance with conventional chemical engineering practice. Moreover the provisions for heat exchange within the illustrated plant are merely one way of achieving the desired temperature levels and any other equivalent system of heat exchange can be used instead.

Referring to the drawing, diethyl maleate is fed in line 1 and admixed with a liquid recycle stream in line 2 containing diethyl succinate, and possibly also gamma-butyrolactone and/or butane-1,4-diol. The combined liquid stream is fed by pump 3 to feed heater 4 in which it is heated to 210° C. by steam supplied in line 5. The resulting hot liquid stream is passed to a spray nozzle 6 in feed saturator 7, in which the resulting spray encounters an ascending stream of hot hydrogen-containing gas supplied in line 8 at 42 bar. Liquid is withdrawn from the bottom of feed saturator 7 in line 9 and is pumped by a feed saturator pump 10 to circulation heater 11 before being sprayed back into feed saturator 7 through nozzle 12. Reference numeral 13 indicates a spray eliminator pad in the top of feed saturator 7. The ester vapour laden stream exits feed saturator 7 in line 14 at a temperature of 166° C. and passes via heat exchanger 15 to a steam heater 16 in which its temperature is raised to 170° C. The $H_2$:ester molar ratio is approximately 300:1. This mixture is then passed under substantially adiabatic reaction conditions through a first bed 17 of copper chromite catalyst containing 25% by weight of copper and 35% by weight of chromium and having a surface area of 85 m$^2$/g. The vaporous reaction mixture exits first bed 17 at an exit temperature of about 185° C. Analysis of this first reaction mixture indicates the absence of diethyl maleate and shows that, besides hydrogen and inert gases (e.g. CO, $CO_2$, methane, propane, $N_2$, A and any other inert gases which may be present in the hydrogen supply to the plant), it contains also significant amounts of diethyl succinate, ethanol, tetrahydrofuran, n-butanol, gamma-butyrolactone, and butane-1,4-diol. In passage through first bed 17 under the substantially adiabatic reaction conditions employed in the process, diethyl maleate is converted smoothly and substantially quantitatively to diethyl succinate, 95.5 mol% of which is then converted to products with a selectivity to ethanol of substantially 100%, a selectivity to tetrahydrofuran of 4.3 mol%, a selectivity to n-butanol of 0.2 mol%, a selectivity to gamma-butyrolactone of 16.0 mol%, and a selectivity to butane-1,4-diol of 79.3 mol%, the balance being minor by-products. Hence the butane-1,4-diol:gamma-butyrolactone molar ratio in this first product mixture from the first hydrogenolysis zone 17 is 4.96:1. The size of the catalyst charge in first bed 17 is preferably selected in relation to the rate of supply of vaporous diethyl maleate thereto so that reaction can proceed substantially to equilibrium in bed 17. The rate of supply of vaporous diethyl maleate to bed 17 corresponds to a liquid hourly space velocity of about 0.45 hr$^{-1}$.

The vaporous first reaction mixture exits first bed 17 at about 185° C. and is passed by way of line 18 to heat exchanger 15, in which it is cooled to 170° C., and is then passed to a second bed 19 of the same copper chromite catalyst. In passage through bed 19 further hydrogenation reactions take place and the reaction mixture reequilibriates to yield a second reaction mixture which exits the second hydrogenolysis zone formed by catalyst bed 19 at a temperature of 171°-172° C. The butane-1,4-diol:gamma-butyrolactone molar ratio in this second reaction mixture is 9:1. The volume of catalyst in the second bed 19 is approximately twice that in the first bed 17; hence the rate at which vaporous diethyl maleate is supplied to bed 17 corresponds to a liquid hourly space velocity, taken over both beds 17 and 19, of about 0.15 hr$^{-1}$.

The second reaction mixture passes in line 20 to a heat exchanger 21 and then to a product cooler 22, in which it is cooled by means of cooling water supplied in line 23, to product catchpot 24. The liquid condensate is recovered in line 25, whilst the gases exit in line 26. The liquid condensate is passed through a pressure let-down valve 27 to a pressure let-down catchpot 28 and thence to a product recovery section 29 in which the product butane-1,4-diol is separated from gamma-butyrolactone, from tetrahydrofuran, from ethanol, from n-butanol, from diethyl succinate, and from any other minor components present in the condensate. Separation of the condensate in product recovery section 29 can be achieved, for example, by distillation in several stages, including a "light ends" distillation stage to remove tetrahydrofuran, ethanol, n-butanol and other low boiling byproducts, and then distillation of the resulting bottoms product to yield an overhead product comprising an azeotrope of gamma-butyrolactone and diethyl succinate and a bottom product comprising butane-1,4-diol. Tetrahydrofuran is recovered in line 30, gamma-butyrolactone in line 31, and butane-1,4-diol in line 32. Diethyl succinate, and possibly also some gamma-butyrolactone and/or butane-1,4-diol, is recycled in line 2.

Fresh hydrogen is supplied to the plant in line 33 and is fed by way of compressor 34 and cooler 35 for admixture with the recycled gas in line 26. The combined gas stream is compressed by recycle compressor 36 and fed to line 8.

A gas purge stream is taken in line 37 after passage through pressure let-down valve 38 and is combined with the vent gas in line 39 from catch pot 28; the combined stream in line 40 passes to gas purge condenser 41 which is fed with refrigerant in line 42 from refrigeration unit 43. The purge gas exits in line 44 whilst any condensate is recovered in line 45 and fed to product recovery section 29. A purge can be taken from the bottom of feed saturator 7 in line 46 as necessary.

Reference numeral 47 indicates a normally closed valve which can be opened at start up of the plant so as to cause the vaporous mixture in line 14 to bypass heat exchanger 15.

If desired, butane-1,4-diol can be passed from the purified butane-1,4-diol product line 32 via line 48 to a dehydration zone 49 which contains a charge of a dehydration catalyst such as gamma-alumina, aluminium phosphate, silica-alumina, a molecular sieve, an acidic clay or similar dehydration catalyst so as to convert at least a proportion of the butane-1,4-diol to tetrahydrofuran. This zone is maintained at a temperature in the range of from about 200° C. to about 300° C. (Alternatively dehydration zone 49 can be supplied with a crude butane-1,4-diol stream from product recovery section 29 in line 50.) The tetrahydrofuran-containing product stream from dehydration section 49 is passed to product recovery section 29 in line 51, thereby increasing the amount of tetrahydrofuran appearing in line 30.

It will readily be appreciated by those skilled in the art that the illustrated plant can, with relatively little modification, be operated using another dialkyl ester of a C$_4$ dicarboxylic acid as feedstock, such as diethyl succinate or a mixture of diethyl maleate and diethyl succinate, in place of diethyl maleate. Some changes to the design of the product recovery section 29 may, however, be required. Such diethyl succinate or a mixture thereof with diethyl maleate may, for example, be produced from diethyl maleate by hydrogenation in an upstream hydrogenation zone (not shown), the product of which is fed to the illustrated plant in line 1.

In an alternative modification of the plant of the drawing diethyl maleate supplied in line 1 is hydrogenated in the vapour phase to diethyl succinate in a hydrogenation zone (not shown) in line 14 upstream from the first hydrogenolysis zone. Such upstream hydrogenation zone contains, for example, a relatively small charge of copper chromite catalyst and the rate of passage of ester therethrough preferably corresponds to a liquid hourly space velocity of at least about 3.0 hr$^{-1}$. Prior to entry to first hydrogenolysis zone 17 the resulting hydrogenated ester containing reaction mixture, which now contains a minor amount only each of diethyl maleate and butane-1,4-diol and a major amount of diethyl succinate, is cooled to remove the heat of hydrogenation of the C:C bond of the unsaturated ester starting material.

We claim:

1. A process for the production of butane-1,4-diol by hydrogenolysis of a dialkyl ester of a C$_4$ dicarboxylic acid characterised in that it comprises:

providing first and second hydrogenolysis zones, each containing a charge of a heterogeneous ester hydrogenolysis catalyst;

supplying to the first hydrogenolysis zone at an elevated pressure and at an elevated first feed temperature in excess of the threshold temperature for the hydrogenolysis reaction a vaporous feed stream comprising a dialkyl ester of a C$_4$ dicarboxylic acid in vapour form and excess hydrogen;

allowing the ester to undergo hydrogenolysis in the first hydrogenolysis zone under substantially adiabatic reaction conditions thereby to form a vaporous first reaction mixture that is substantially free from the starting ester and contains, in addition to unreacted hydrogen, butane-1,4-diol and gamma-butyrolactone in a first molar ratio;

cooling the vaporous first reaction mixture;

supplying a second vaporous feed stream comprising resulting cooled vaporous first reaction mixture to the second hydrogenolysis zone at a second feed temperature in excess of the threshold temperature for the hydrogenolysis reaction;

allowing the second vaporous feed stream to react further and to equilibrate under substantially adiabatic reaction conditions in the second hydrogenolysis zone; and recovering from the second hydrogenolysis zone a vaporous second reaction mixture containing, in addition to unreacted hydrogen, butane-1,4-diol and gamma-butyrolactone in a second molar ratio that is greater than the first molar ratio.

2. A process according to claim 1, characterised in that the heterogeneous hydrogenolysis catalyst comprises copper chromite.

3. A process according to claim 2, characterised in that the copper chromite catalyst contains, before reduction, from about 25 to about 45% by weight of copper and from about 20 to about 35% by weight of chromium.

4. A process according to claims 1, 2 or 3, characterised in that the first feed temperature ranges from about 150° to about 200° C.

5. A process according to claim 4, characterised in that the first feed temperature is from about 170° to about 190° C.

6. A process according to claim 1, characterised in that the vaporous first reaction mixture is recovered from the first hydrogenolysis zone at a temperature in the range of from about 170° to about 200° C.

7. A process according to claim 1, characterised in that the second feed temperature is at least about 5° C. lower than the temperature at which the vaporous first reaction mixture exits the first hydrogenolysis zone.

8. A process according to claim 1, characterised in that the second feed temperature lies in the range of from about 150° C. to about 190° C.

9. A process according to claim 1, characterised in that the hydrogen:ester molar ratio in the first vaporous feed stream is in the range of from about 100:1 to about 800:1.

10. A process according to claim 1, characterised in that the first feed temperature is at least about 5° C. above the dew point of the first vaporous feed stream.

11. A process according to claim 1, characterised in that the second feed temperature is at least about 5° C. above the dew point of the second vaporous feed stream.

12. A process according to claim 1, characterised in that the pressure lies in the range of from about 25 bar to about 70 bar.

13. A process according to claim 1, characterised in that the ester is fed to the first hydrogenolysis zone at a rate corresponding to a liquid hourly space velocity of from about $0.1$ $hr^{-1}$ to about $3.0$ $hr^{-1}$.

14. A process according to claim 1, characterised in that the ester is a di-($C_1$ to $C_4$ alkyl) ester of a $C_4$ dicarboxylic acid.

15. A process according to claim 14, characterised in that the ester is selected from diethyl maleate, dialkyl fumarate and mixture thereof.

16. A process according to claim 14, characterised in that the ester is selected from diethyl succinate, and mixtures thereof with one or both of diethyl maleate and diethyl fumarate.

* * * * *